US009999439B2

(12) United States Patent
Duperier et al.

(10) Patent No.: US 9,999,439 B2
(45) Date of Patent: *Jun. 19, 2018

(54) LAPAROSCOPIC SCALPEL AND METHOD FOR USE

(71) Applicant: Dsign Surgical Innovations, LLC, San Antonio, TX (US)

(72) Inventors: Frank Dauterive Duperier, San Antonio, TX (US); Michael Vollentine Seger, San Antonio, TX (US)

(73) Assignee: DSIGN SURGICAL INNOVATIONS, LLC, San Antonio, TX (US)

( * ) Notice: Subject to any disclaimer, the term of this patent is extended or adjusted under 35 U.S.C. 154(b) by 223 days.

This patent is subject to a terminal disclaimer.

(21) Appl. No.: 14/923,136

(22) Filed: Oct. 26, 2015

(65) Prior Publication Data

US 2016/0106452 A1    Apr. 21, 2016

Related U.S. Application Data

(63) Continuation of application No. 14/053,331, filed on Oct. 14, 2013, now Pat. No. 9,168,058, which is a (Continued)

(51) Int. Cl.
*A61B 17/3211* (2006.01)
*A61B 17/34* (2006.01)
(Continued)

(52) U.S. Cl.
CPC .... *A61B 17/3211* (2013.01); *A61B 17/00234* (2013.01); *A61B 17/3209* (2013.01); *A61B 17/3417* (2013.01); *A61B 19/46* (2013.01); *A61B 2017/0042* (2013.01); *A61B 2017/0046* (2013.01); *A61B 2017/00424* (2013.01); (Continued)

(58) Field of Classification Search
CPC .......... A61B 17/3211; A61B 17/00234; A61B 17/3209; A61B 17/32093; A61B 17/3417; A61B 2017/32113; A61B 2017/32116; A61B 2017/3213; A61B 2017/00424; A61B 2017/00455; A61B 2017/0046; A61B 2017/0042
See application file for complete search history.

(56) References Cited

U.S. PATENT DOCUMENTS 314,507 A    3/1885   Yonge ............................. 7/160
453,296 A    6/1891   Tata
(Continued)

OTHER PUBLICATIONS

Fox, "Fox Knives, FOX64022B T-handle Knife" p. 1 (as early as 2009).
(Continued)

*Primary Examiner* — Jocelin Tanner
(74) *Attorney, Agent, or Firm* — David G. Rosenbaum; J. Peter Paredes; Rosenbaum IP, P.C.

(57) ABSTRACT

A laparoscopic scalpel includes a shaft and a recess disposed in a surface of the shaft proximal to a distal end of the shaft. A blade is attached to the shaft. The blade includes a cutting edge having a portion exposed by the recess and oriented outwardly from the recess. A proximal end of the portion of the cutting edge exposed by the recess is disposed further from the surface than is a distal end of the portion of the cutting edge exposed by the recess.

20 Claims, 8 Drawing Sheets

Related U.S. Application Data continuation of application No. 13/035,598, filed on Feb. 25, 2011, now Pat. No. 8,585,725.

(51) Int. Cl.
*A61B 17/3209* (2006.01)
*A61B 19/00* (2006.01)
*A61B 17/00* (2006.01)
*A61B 90/00* (2016.01)

(52) U.S. Cl.
CPC .......... *A61B 2017/00455* (2013.01); *A61B 2019/462* (2013.01); *A61B 2090/0811* (2016.02)

(56) References Cited

U.S. PATENT DOCUMENTS

| | | | |
|---|---|---|---|
| 1,135,987 A | 4/1915 | Beecher | |
| 1,522,298 A | 1/1925 | Goodrich | 30/29.5 |
| 1,831,579 A | 11/1931 | Sneed | 30/29.5 |
| 1,987,514 A | 1/1935 | Marusich | 30/32 |
| 2,267,934 A | 12/1941 | Lockett | 30/294 |
| 4,491,132 A | 1/1985 | Aikins | 128/305 |
| 4,604,804 A | 8/1986 | Sparks | 30/294 |
| 5,029,573 A | 7/1991 | Chow | 128/4 |
| 5,122,152 A | 6/1992 | Mull | 606/170 |
| 5,176,695 A | 1/1993 | Dulebohn | 606/170 |
| 5,215,521 A | 6/1993 | Cochran et al. | 604/22 |
| 5,269,796 A | 12/1993 | Miller et al. | 606/167 |
| 5,282,816 A | 2/1994 | Miller et al. | 606/167 |
| 5,331,971 A | 7/1994 | Bales et al. | 128/751 |
| 5,341,822 A | 8/1994 | Farr et al. | 128/898 |
| 5,449,355 A | 9/1995 | Rhum et al. | 606/41 |
| 5,507,800 A | 4/1996 | Strickland | 606/167 |
| 5,628,760 A | 5/1997 | Knoepfler | 606/170 |
| 5,667,519 A | 9/1997 | Ramsey | 606/167 |
| 5,964,037 A | 10/1999 | Clark | 30/223 |
| 6,007,554 A | 12/1999 | Van Ess | 606/167 |
| 6,051,005 A | 4/2000 | Brandsey et al. | 606/148 |
| 6,077,284 A | 6/2000 | Piraka | 606/167 |
| 6,270,501 B1 | 8/2001 | Freiberg et al. | 606/79 |
| 6,500,187 B1 | 12/2002 | Petersen | 606/167 |
| 7,458,966 B2 | 12/2008 | Frank et al. | 606/1 |
| 8,273,098 B2 | 9/2012 | Strickland | 606/170 |
| 8,585,725 B2 * | 11/2013 | Duperior | A61B 17/3211 606/170 |
| 9,168,058 B2 * | 10/2015 | Duperier | A61B 17/3211 |
| 2004/0176789 A1 | 9/2004 | Lee et al. | 606/170 |
| 2004/0237312 A1 | 12/2004 | Hernandez et al. | 30/162 |
| 2005/0193564 A1 | 9/2005 | Trbovich, Jr. | 30/115 |
| 2008/0045987 A1 | 2/2008 | Lee et al. | 606/159 |
| 2008/0243158 A1 | 10/2008 | Morgan | 606/167 |
| 2009/0198263 A1 | 8/2009 | LaFauci et al. | 606/167 |
| 2010/0100111 A1 | 4/2010 | Rogerson | 606/167 |
| 2010/0185223 A1 | 7/2010 | Rogerson | 606/170 |

OTHER PUBLICATIONS

LiNA, "LiNA fascia scalpel: single use instrument for safe enlargement of trocar incisions" http://www.dma.no/uploads/lina_fascia_scalpel.pdf pp. 1-2 (2009).
PCT International Search Report issued in a corresponding foreign application, PCT/US2012/024736, pp. 1-7 (dated Aug. 24, 2012).
PCT International Preliminary Report on Patentability issued in a corresponding foreign application, pp. 1-6 (dated Sep. 6, 2013).

* cited by examiner

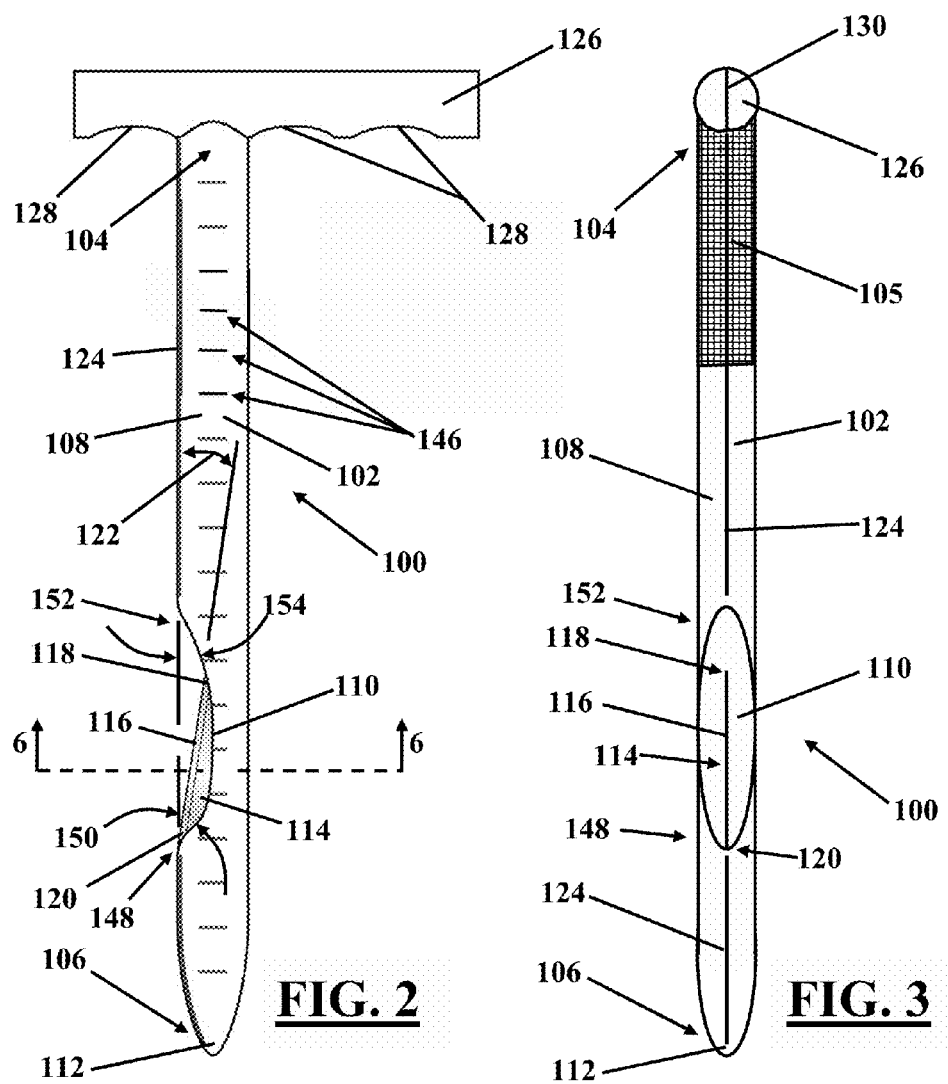

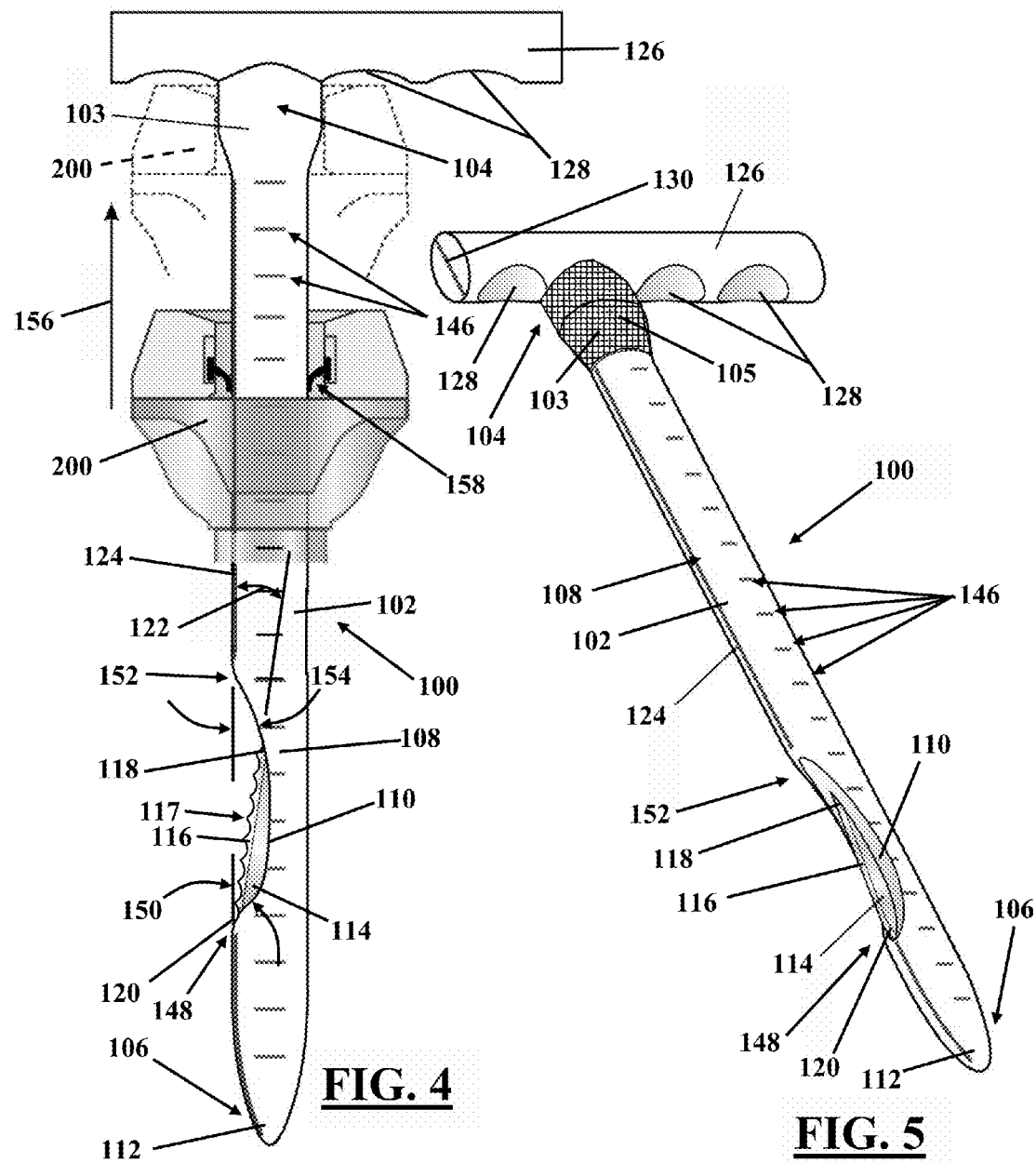

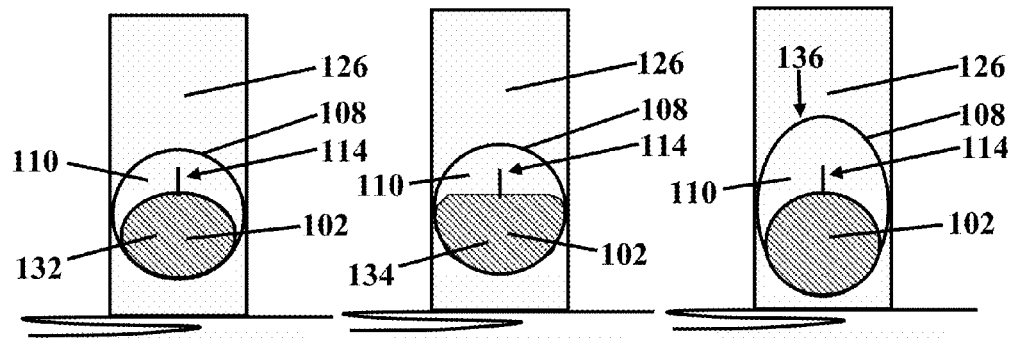
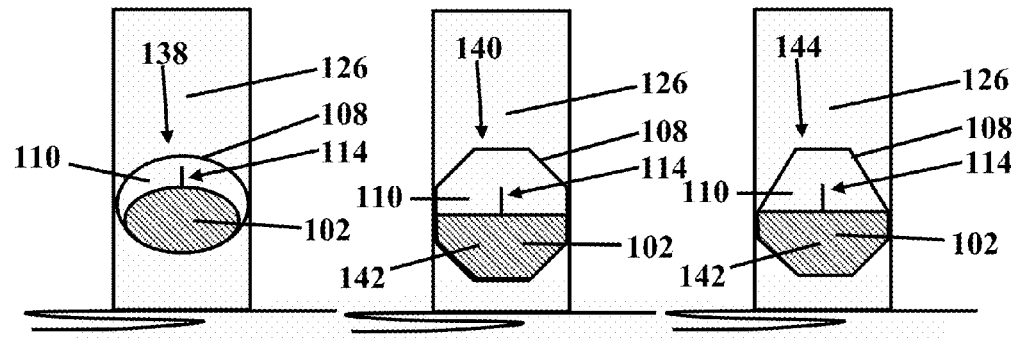
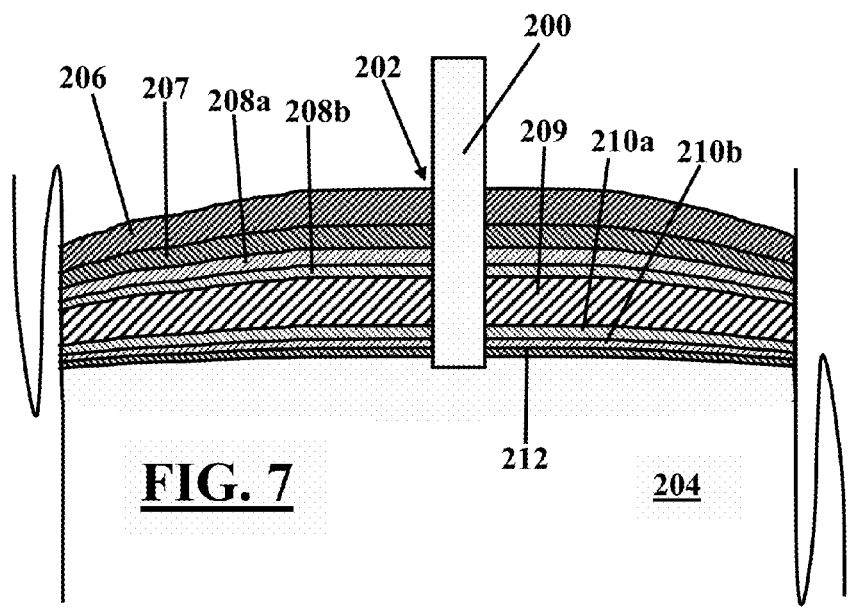

LAPAROSCOPIC SCALPEL AND METHOD FOR USE

CROSS-RELATED APPLICATIONS

The present application claims priority from and is a continuation from U.S. patent application Ser. No. 14/053,331, filed Oct. 14, 2013, now U.S. Pat. No. 9,168,058, which claims priority from and is a continuation from U.S. patent application Ser. No. 13/035,598, filed Feb. 25, 2011, which is now U.S. Pat. No. 8,585,725, all of which are herein incorporated by reference in their entireties.

FIELD OF THE INVENTION

The present invention relates generally to a laparoscopic surgical device. More particularly, the present invention relates to a laparoscopic scalpel that facilitates enlargement of a laparoscopic incision through the peritoneum, fascia, and abdominal wall muscles for extraction of solid organs or other specimens, and/or introduction of intraluminal staplers or other devices.

BACKGROUND OF THE INVENTION

Laparoscopic surgery, also known as "minimally invasive" surgery, is a method for performing surgery via one or more small incisions typically on the order of about 1 cm across.

It is known that laparoscopic surgery offers many benefits to patients and the healthcare system including, for example, less pain, shorter hospital stay, quicker return to normal activity and to work, and better cosmetic results. These benefits make the health care system more efficient; thus laparoscopic techniques are in high demand.

Laparoscopic surgery has revolutionized patient care in the last 20 years. In many cases, minimally invasive approaches have become the standard care, even for specialties such as gynecology, urology, kidney transplant, and foregut surgery. In 2010, there were 2.8 million minimally invasive procedures performed in the United States alone, representing an increase of about 2.6% from 2009. However, these procedures include only about 38% of colectomies and 25% of hysterectomies being performed in a minimally invasive fashion. Furthermore, these procedures do not include the usage of the current inventive device in procedures such as adrenalectomy, gastrectomy, donor and pathological nephrectomies, prostates, and liver resections. Therefore, the number of minimally invasive procedures is expected to continue to rise as technology expands.

Furthermore, with the advent of 'robotic' surgery more and more techniques are being created. In the past, many surgeons abstained from laparoscopic or robotic techniques because it was felt to not offer an advantage if solid organs required extraction. For example, if a surgeon was doing a colon resection, it was not uncommon for surgeons to perform the operation in an 'open' fashion or quickly convert from laparoscopic to open knowing that they were going to require an open incision to extract the solid organ in question.

As more intra-abdominal surgery is being offered with minimally invasive techniques, surgeons need to have the ability to extract a specimen, for example a solid organ, either whole or morcellated. To facilitate the removal of larger solid organs such as, for example, kidneys, adrenals, the uterus, colon, small bowel, gallbladder, and tumors, a surgeon has to create a sufficiently wide extraction site on the peritoneal surface of the abdominal wall. However, in order to preserve the integrity of the minimally invasive operation, surgeons strive to remove the specimen through the smallest possible skin incision. Therefore, a problem may arise when a specimen needing to be removed is larger than any of the laparoscopic incisions.

Currently, there is no reliable 'sharp' option available for lengthening a laparoscopic incision. For example, if an organ requires extraction, the skin is cut with a scalpel; however, the fascia, muscle, and peritoneum are all bluntly 'ripped' and spread apart by the surgeon's fingers or a blunt instrument to allow for extraction of the organ. This blunt method, while adequate, is imprecise, takes increased time to execute, and leads to a considerable amount of tissue trauma, causing increased postoperative pain. In addition, this blunt method leads to the instant loss of the pneumoperitoneum, which is gas normally sealed within the body cavity. Such loss of the pneumoperitoneum may result in a massive expulsion of carbon dioxide gas and aerosolized body fluid when the organ is removed under pressure of the pneumoperitoneum. Such expulsion may expose the surgeons and operating room technologists to an infectious disease hazard and therefore is a safety issue.

Although not widely used, a "fascia scalpel" manufactured by LiNA Medical in Glostrup, Denmark, is designed to be inserted next to a specimen bag which is being pulled up against the abdominal wall. This creates problems as the bag will tend to surround and engulf the LiNA scalpel, and the specimen bag can be cut which can lead to loss of integrity of the bag, loss of containment of the specimen, and potential dissemination of contaminated fluid, for example, an infected appendix, or cancerous cells, for example, a malignant tumor. Thus, the LiNA scalpel is designed for cutting more superficially on the abdominal wall or the more dorsal part of the skin and is not designed for the more ventral part of the abdominal wall. The LiNA fascia scalpel is designed for use with smaller solid organs like the appendix and/or gallbladder. The LiNA fascia scalpel is not designed to be placed through a trocar, nor does the LiNA scalpel have a blunt distal end to protect tissue from unintended damage. Additionally, the LiNA fascia scalpel does not enable surgeons to use the instrument under visualization nor does it allow surgeons to work without releasing the pneumoperitoneum.

Further issues exist with using a traditional surgical scalpel to enlarge a laparoscopic incision. For example, when using a regular surgical scalpel attached to a standard or longer handle, it is possible that the scalpel blade may be dislodged from the handle by the abdominal wall tissue and/or the rubber housing of existing trocars if the scalpel is introduced inside the trocar. In addition, standard cutting with a scalpel is not protected and surrounding tissues can be unintentionally injured. Further, a traditional surgical scalpel or a LiNA fascia scalpel can slip and fall freely into the abdomen creating an enterotomy (bowel injury) and thus have potentially devastating consequences.

A need exists for a laparoscopic scalpel that can precisely enlarge a laparoscopic incision without compromising the pneumoperitoneum. Such a device would safely, quickly, and efficiently incise the peritoneum, fascia, and abdominal wall muscles to extract solid organs or introduce intraluminal staplers or other devices. Such a device would allow for extraction of larger specimens, which allows for wider applicability across multiple specialties including, but not limited to urology, gynecology, general surgery, bariatric surgery, endocrine surgery, colorectal surgery, liver surgery, and thoracoscopic surgery of the chest.

SUMMARY OF THE INVENTION

In one aspect of the present invention, a laparoscopic scalpel includes a shaft and a recess disposed in a surface of the shaft proximal to a distal end of the shaft. A blade is attached to the shaft. The blade includes a cutting edge having a portion exposed by the recess and oriented outwardly from the recess. A proximal end of the portion of the cutting edge exposed by the recess is disposed further from the surface than is a distal end of the portion of the cutting edge exposed by the recess.

In another aspect of the present invention, a laparoscopic scalpel includes a shaft and a recess disposed in a surface of the shaft proximal to a distal end of the shaft. A blade is attached to the shaft. The blade includes a cutting edge having a portion exposed by the recess and oriented outwardly from the recess. A proximal end of the portion of the cutting edge exposed by the recess is disposed further from the surface than is a distal end of the portion of the cutting edge exposed by the recess. A handle is disposed on a proximal end of the shaft and extends from the shaft along a plane that is generally parallel to the cutting edge.

In a further aspect of the present invention, a method for using a laparoscopic scalpel is presented. The laparoscopic scalpel includes a shaft, a recess disposed in a surface of the shaft proximal to a distal end of the shaft, and a blade attached to the shaft. The blade includes a cutting edge having a portion exposed by the recess and oriented outwardly from the recess. The portion of the cutting edge exposed by the recess is disposed at a non-zero angle relative to the surface. The shaft is adapted to be inserted through a trocar into a patient while generally maintaining the patient's pneumoperitoneum. The method includes the steps of inserting a distal end of the shaft into a trocar disposed within a laparoscopic incision, translating the trocar proximally relative to the shaft to expose one or more of the fascia, muscle, and peritoneum to the cutting edge while generally maintaining the patient's pneumoperitoneum, and cutting the one or more of the fascia, muscle, and peritoneum or other dorsal part of the abdominal wall with the cutting edge to enlarge the laparoscopic incision without compromise of the patient's pneumoperitoneum.

The foregoing and other features and advantages are defined by the appended claims. The following detailed description of exemplary embodiments, read in conjunction with the accompanying drawings is merely illustrative rather than limiting, the scope being defined by the appended claims and equivalents thereof.

BRIEF DESCRIPTION OF THE DRAWINGS

In the accompanying figures, like elements are identified by like reference numerals among the several preferred embodiments of the present invention.

FIG. 2 illustrates a side elevation of the laparoscopic scalpel of FIG. 1.

FIG. 3 illustrates a side elevation of another embodiment of a laparoscopic scalpel.

FIG. 4 illustrates a side elevation of a further embodiment of a laparoscopic scalpel disposed in relation to a proximal end of a trocar.

FIG. 5 illustrates an isometric view of yet another embodiment of a laparoscopic scalpel.

FIGS. 6A-6F illustrate cross-sectional views of embodiments of a laparoscopic scalpel taken generally along the lines 6-6 of FIG. 2.

FIG. 7 illustrates a cross-sectional view of a trocar disposed through layers of tissue.

DETAILED DESCRIPTION OF THE DRAWINGS

The foregoing and other features and advantages of the invention are apparent from the following detailed description of exemplary embodiments, read in conjunction with the accompanying drawings. The detailed description and drawings are merely illustrative of the invention rather than limiting, the scope of the invention being defined by the appended claims and equivalents thereof.

Language indicative of a relative geometric relationship between components includes use of the terms "proximal" and "distal" herein. In this context, "proximal" refers to an end of a component nearest to the medical practitioner during use and "distal" refers to the end of the component furthest from the medical practitioner during use.

Figure 1:
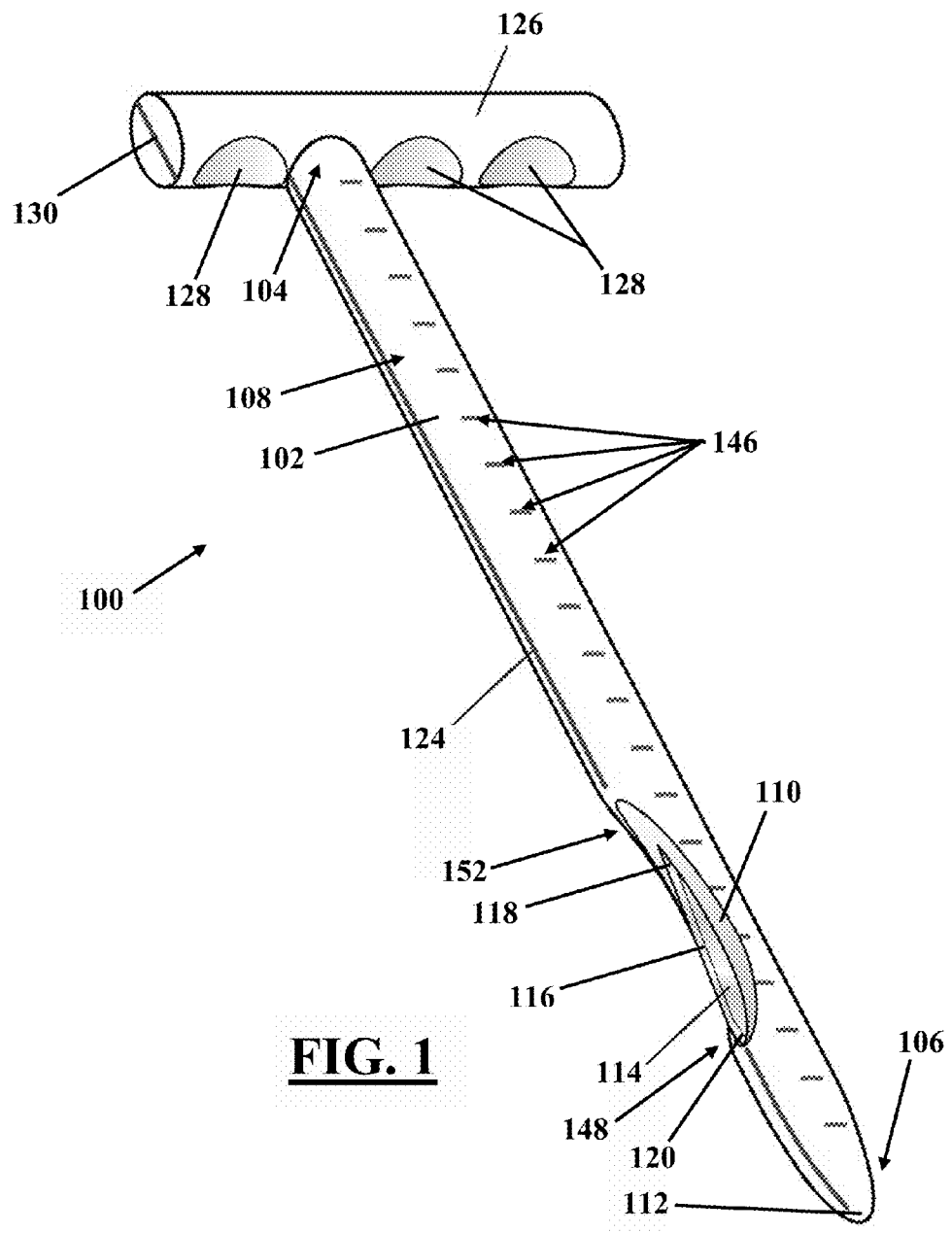
FIG. 1 illustrates an isometric view of an embodiment of a laparoscopic scalpel.

Referring to FIGS. 1-3, in one embodiment, a laparoscopic scalpel 100 includes a shaft 102 having a proximal end 104, a distal end 106 and a surface 108. A recess 110 is disposed in the surface 108 of the shaft 102 proximal to the distal end 106 of the shaft 102. In one embodiment, the distal end 106 has a blunt end surface 112. A blade 114 is attached to the shaft 102 and includes a cutting edge 116. In one embodiment, the cutting edge 116 may include serrations 117, as illustrated in FIG. 4. The blade 114 may be attached to the shaft by any method as known in the art, including by way of example and not limitation, being overmolded by the material of the shaft, attached to the shaft via a fastener, and being constructed integrally from the same material as the shaft.

The blade is disposed relative to the shaft such that a portion of the cutting edge 116 is exposed by the recess 110 and is oriented outward relative to the recess 110. The portion of the cutting edge 116 exposed by the recess 110 includes a proximal end 118 and a distal end 120. In one embodiment, the cutting edge 116 is linear between the proximal and distal ends 118, 120. In other embodiments, the cutting edge 116 may be convex, concave, or a combination of convex, concave and/or linear between the proximal and distal ends 118, 120. As will be more fully described hereinbelow, in one embodiment, the proximal end 118 may be disposed further from the surface 108 than is the distal end 120. In this embodiment, if the cutting edge 116 is linear, there results a non-zero angle 122 (See FIG. 2) between the cutting edge 116 and a region of the surface 108 replaced by the recess 110.

Because no portion of the blade 114 extends beyond the surface 108, the blade 114 may be completely shielded by any tube or shield that can be fit over the shaft 102. Such protection provides safety against unintentional application of the cutting edge 116 to tissue. Configuration of the recess 110 proximal to the distal end 106 of the shaft 102 provides a region of the surface 108 between the blade 114 and the distal end 106 of the shaft 102. Such configuration may provide further safety against an end of the blade 114 extending to near or past the distal end 106.

In another embodiment, the surface 108 near the proximal end 104 of the shaft 102 may include a rubberized or otherwise textured and/or compressible material 105, as illustrated by the cross-hatched region in FIG. 3. In another embodiment, the proximal end 104 of the shaft 102 may include a tapered or enlarged portion 103, as illustrated in FIG. 4. In a further embodiment, the proximal end 104 of the shaft 102 includes the enlarged portion 103 including the rubberized or otherwise textured and/or compressible material 105, as illustrated by the cross-hatched region in FIG. 5. The enlarged portion 103 and/or the material 105 may facilitate anchoring or docking a trocar or sheath 200 (See FIG. 4) to the proximal end 104, such as for example, when the trocar 200 is slid proximally relative to the shaft 102 as illustrated by arrow 156 in FIG. 4. Such docking may help to stabilize the trocar or sheath 200 while operating the laparoscopic scalpel 100.

Referring to FIGS. 1-5, in another embodiment, an edge guide 124 may be disposed longitudinally along the surface 108 generally aligned with the cutting edge 116. The edge guide 124 provides an indication of the direction that the cutting edge 116 is facing when the cutting edge 116 is not visible to the surgeon, for example, when the laparoscopic scalpel 100 is inserted into a trocar or other sleeve 200 (See FIGS. 7-13). The edge guide 124 may be a visible line on the surface 108, and/or may include a tactile component such as a raised rib or groove along the surface 108. The addition of a tactile component may be helpful to a surgeon in the event that the surface 108 becomes obscured by fluid or other material.

In a further embodiment of the laparoscopic scalpel 100, a handle 126 is disposed on the proximal end 104 of the shaft 102. As will be more fully explained hereinbelow, the handle 126 is oriented transversely to the shaft 102, as illustrated in FIGS. 1, 2, 4, and 5. In one embodiment, the handle 126 extends transversely from the shaft 102 in a direction that is generally normal to the edge guide 124. In another embodiment, the handle 126 is disposed on the proximal end 104 of the shaft 102 and extends transversely from the shaft 102 along a plane that is generally parallel to the cutting edge 116. In a further embodiment, the handle 126 is detachably disposed on the proximal end 104 of the shaft 102. Such detachable attachment may be via a press fit, a snap fit, a threaded attachment, a bayonet attachment, matching of a particular shaped rib and groove, and the like.

Transverse extension of the handle 126 relative to the shaft 102 may provide a medical professional with additional leverage or an improved angle for grasping the handle 126. Such additional leverage or improved grasping angle may facilitate easier manipulation of the blade 114 disposed proximate the distal end 106 of the shaft 102 opposite the handle 126. Transverse extension of the handle 126 also provides a safety feature as will be further described hereinbelow.

In one embodiment, the handle 126 may further include finger grips 128 disposed thereon to facilitate an improved grip on the handle 126 by a medical professional. In yet another embodiment, instead of or in addition to the edge guide 124 that is disposed longitudinally along the surface 108, an edge guide 130 may be disposed on an edge of the handle 126 in general alignment with the cutting edge 116, as illustrated in FIGS. 1 and 3-5. Similar to the edge guide 124, the edge guide 130 may be a visible line and/or may include a tactile component such as a raised rib or groove.

Referring to FIGS. 6A-6F, the shaft 102 of the laparoscopic scalpel 100 may have any cross-sectional shape disposed in any orientation relative to the handle 126 as desired. Further, the shaft 102 may include any cross-sectional shape in regions outside of the recess 110 combined with any cross-sectional within the bounds of the recess 110. For example, referring to FIG. 6A, the shaft 102 may have a generally round cross-sectional shape outside of the recess 110 as indicated by the generally round surface 108, and may have a generally elliptical shape 132 within the bounds of the recess 110. Referring to FIG. 6B, for example, the shaft 102 may have a generally semi-circular shape 134 within the bounds of the recess 110. In other embodiments, the shaft may have an elliptical or oval shape 136 that has a long axis thereof aligned with the blade 114, as illustrated in FIG. 6C. Alternatively, the shaft 102 may have an elliptical or oval shape 138 having a short axis thereof aligned with the blade 114, as illustrated in FIG. 6D.

The shaft 102 may have other cross-sectional shapes and orientations, including without limitation, any closed curvilinear shape such as generally round, elliptical, or oval, any regular polygonal shape, and any irregular polygonal shape. For example, referring to FIG. 6E, the shaft 102 is illustrated as having a regular octagonal shape 140 in regions outside of the recess 110. Within the recess 110, the shaft is illustrated as having a half-regular octagonal shape 142. In another example, referring to FIG. 6F, the shaft 102 has an irregular polygonal shape including seven sides of uneven length 144 in regions outside the recess 110, yet has the half-regular octagonal shape 142 within the recess 110.

In another embodiment, the laparoscopic scalpel 100 may include regularly spaced distance markings 146 disposed along the surface thereof, as illustrated in FIGS. 1-5. As will be described more fully hereinbelow, the distance markings indicate a depth of insertion of the shaft 102 when inserted into a trocar or other sleeve 200 (See FIGS. 7-13). The distance markings 146 may be visible lines on the surface 108, and/or may include a tactile component such as raised ribs or grooves along the surface 108. Similar to the edge guides 124, 130, the addition of a tactile component to the distance markings 146 may be helpful to a surgeon in the event that the surface 108 becomes obscured by fluid or other material.

Any of the various embodiments of the laparoscopic scalpel described hereinabove with regard to FIGS. 1-6F may be used to enlarge a laparoscopic incision without losing a patient's pneumoperitoneum. For example, referring to FIG. 7, a trocar or sealing sheath 200 is illustrated inserted via an incision 202 through the various layers of tissue into a body cavity 204. The trocar 200 includes a seal (for example, reference numeral 158 illustrated in FIG. 4) through which other surgical tools may be passed without disturbing the seal. Thus, the interior of the trocar 200 may be exposed to a patient's pneumoperitoneum upon insertion of the trocar 200 as illustrated in FIG. 7. However, the seal inhibits release of the patient's pneumoperitoneum from within the trocar 200.

The various layers of tissue present at a point of entry into the body cavity 204 differ depending on location of the incision 202. For example, a typical cross-sectional profile of layers in the abdominal region includes, for example, skin 206, subcutaneous tissue (mainly fat) 207, ventral fascia 208 including superficial fascia 208a and deep fascia 208b, multiple layers of muscle 209, dorsal fascia 210 including transversalis fascia 210a and subserous fascia 210b, and the peritoneum 212. Of course, each of these layers may include one or more sublayers or additional layers as known in the art.

Figure 8:
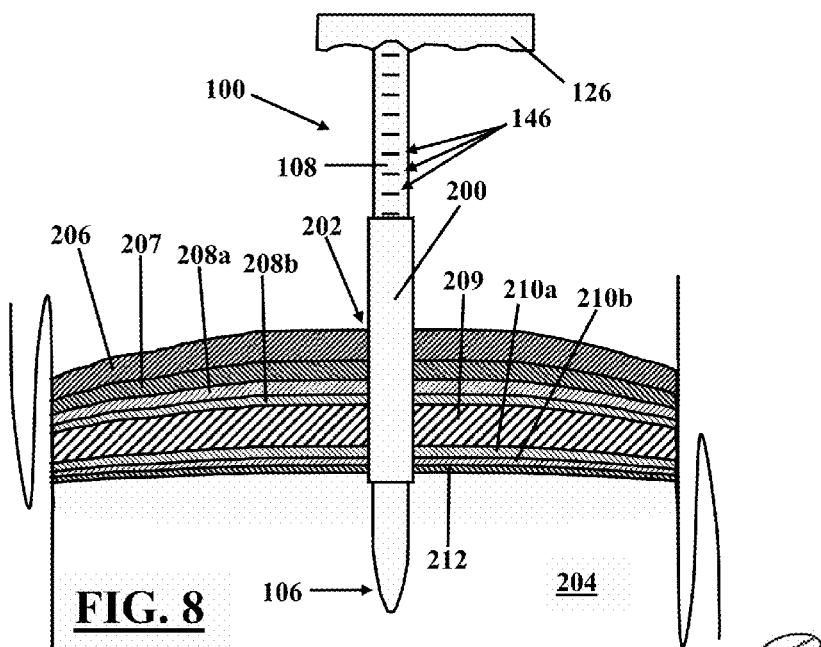
FIG. 8 illustrates a cross-sectional elevational view of insertion of an embodiment of the laparoscopic scalpel of the current invention into a body cavity via a trocar.
Figure 9:
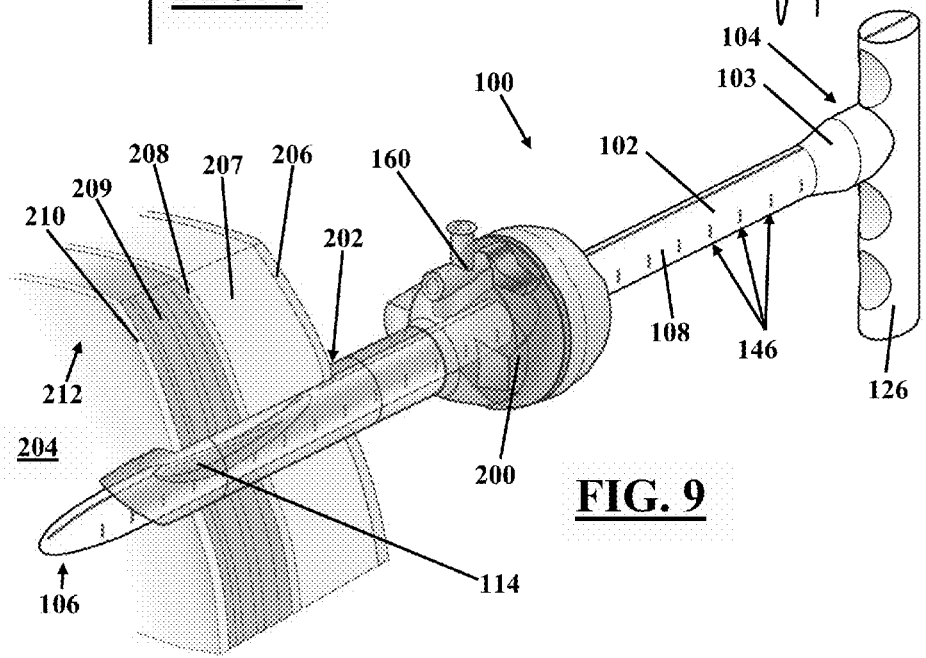
FIG. 9 illustrates a cross-sectional isometric view of insertion of another embodiment of the laparoscopic scalpel of the current invention into a body cavity via a trocar.
Figure 10:
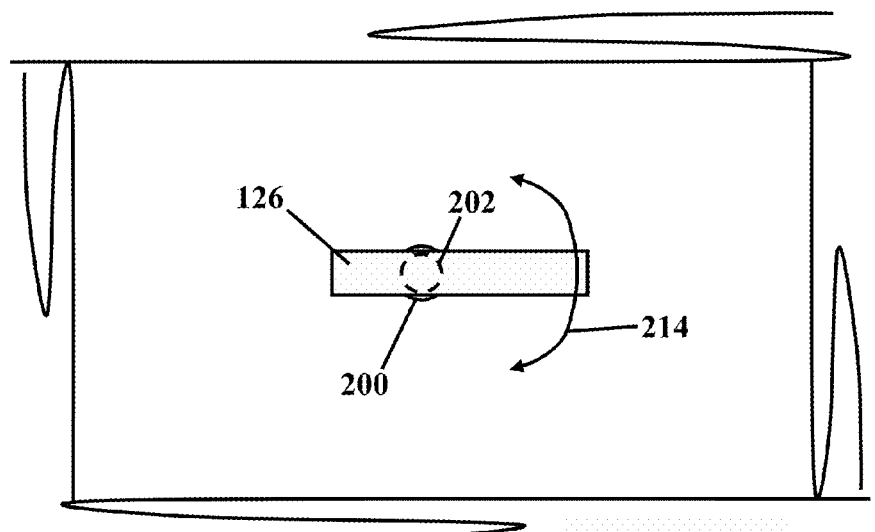
FIG. 10 illustrates rotationally orienting the laparoscopic scalpel of the current invention following insertion thereof into a trocar.

Referring to FIGS. 8 and 9, in one embodiment of a method for use of the laparoscopic scalpel 100, the distal end 106 of the shaft 102 is inserted into the trocar or shield 200 already in place within the incision 202 as illustrated in FIG. 7. In one embodiment, as noted hereinabove with regard to FIGS. 1-5, the distance markings 146 disposed along the surface 108 of the shaft 102 provide an indication of depth of insertion of the shaft 102 when inserted through the trocar 200. When using an embodiment including the distance markings 146, the step of inserting the distal end of the shaft 102 may further include inserting the distal end of the shaft 102 into the trocar 200 to a desired depth of insertion. The desired depth of insertion may be determined by the desired depth of the blade 114 relative to one or more of the layers of tissue 206, 207, 208a, 208b, 209, 210a, 210b, 212, or via other determinations as known in the art.

As noted hereinabove with regard to FIGS. 1-5, in one embodiment, the handle 126 extends transversely from the shaft 102 along a plane that is generally parallel to the cutting edge 116. In another embodiment, the handle 126 extends transversely from the shaft 102 in a direction that is generally normal to the edge guide 124, which may be generally aligned with the cutting edge 116. In a further embodiment, the second edge guide 130 disposed on an edge of the handle 126 may be in general alignment with the cutting edge 116. Thus, the rotational orientation of the handle 126 is consistent with the rotational orientation of the cutting edge 116, such that following insertion of the laparoscopic scalpel 100 into the trocar 200, the cutting edge may be oriented rotationally as desired by rotationally adjusting the position of the handle 126, as illustrated by arrows 214 in FIG. 10.

As noted hereinabove with regard to FIGS. 1-5, transverse extension of the handle 126 also provides a safety feature. Referring to FIGS. 8 and 9, for example, should the laparoscopic scalpel 100 slip from the grasp of a surgeon, the transverse extension of the handle 126 inhibits the laparoscopic scalpel 100 from falling freely into the abdomen or body cavity 204 and possibly creating an enterotomy (bowel injury) having potentially devastating consequences.

Referring to FIGS. 8 and 9, upon placement of the laparoscopic scalpel 100 at the desired depth and orientation within the trocar 200, the blade 114 is not exposed to tissue but is shielded from surrounding tissue by the trocar 200. For illustration purposes, the trocar 200 in FIG. 9 has been drawn as transparent to show the position of the blade 114 therein. Such shielding is an improvement over cutting with existing scalpels, which are not protected and which may thereby cause unintentional injury to tissue.

Figure 11:
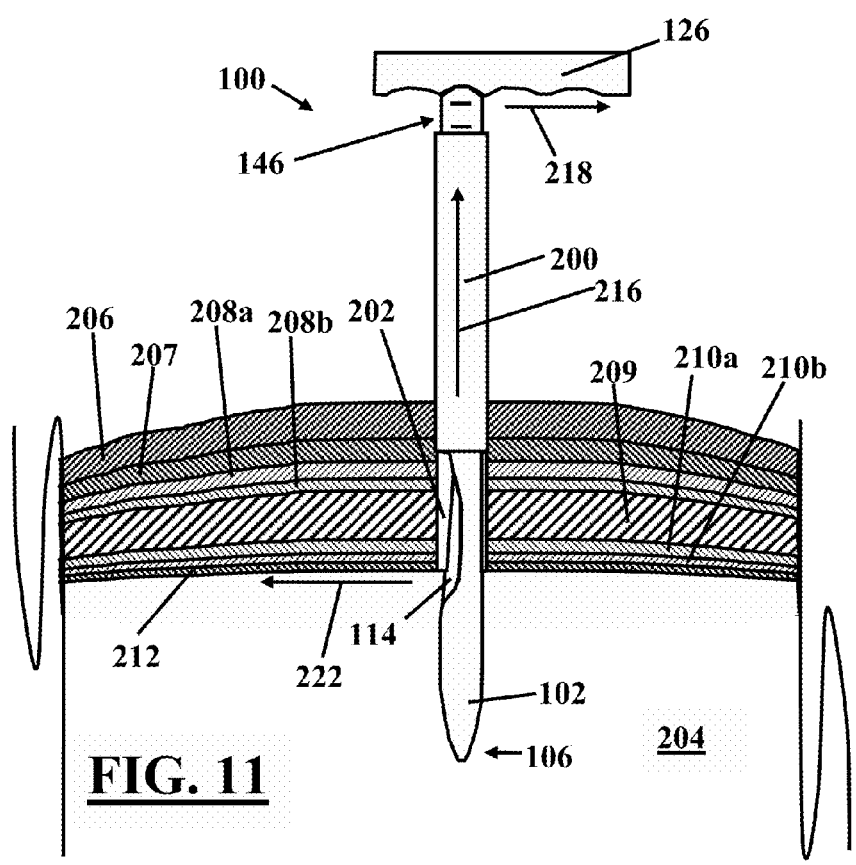
FIG. 11 illustrates lateral and proximal manipulation of the laparoscopic scalpel of the current invention relative to an incision.

The cutting edge 116 of the blade 114 is exposed to tissue by translating the trocar 200 proximally relative to the shaft 102, as illustrated by arrow 216 in FIG. 11. The trocar 200 may be translated as desired to expose one or more of the layers of tissue 206, 207, 208a, 208b, 209, 210a, 210b, 212 as desired while generally maintaining the patient's pneumoperitoneum. For example, as illustrated in FIG. 11, the trocar 200 has been translated proximally relative to the shaft 102 to expose the peritoneum 212, the dorsal fascia layers 210, the layers of muscle 209, and the ventral fascia layers 208 to the cutting edge 116 of the blade 114; however, the trocar 200 maintains a seal with the layer of skin 206 and the layer of subcutaneous tissue 207, thereby maintaining the patient's pneumoperitoneum.

Upon exposure of one or more of the layers of tissue 206, 207, 208a, 208b, 209, 210a, 210b, 212 as desired, the next step is to radially enlarge a dorsal portion of the incision 202 without compromise of the patient's pneumoperitoneum. This may be accomplished by creating a pyramidal type incision 202 that is largest at the most dorsal part of the abdominal wall and that is smallest as it nears the skin level.

Figure 12:
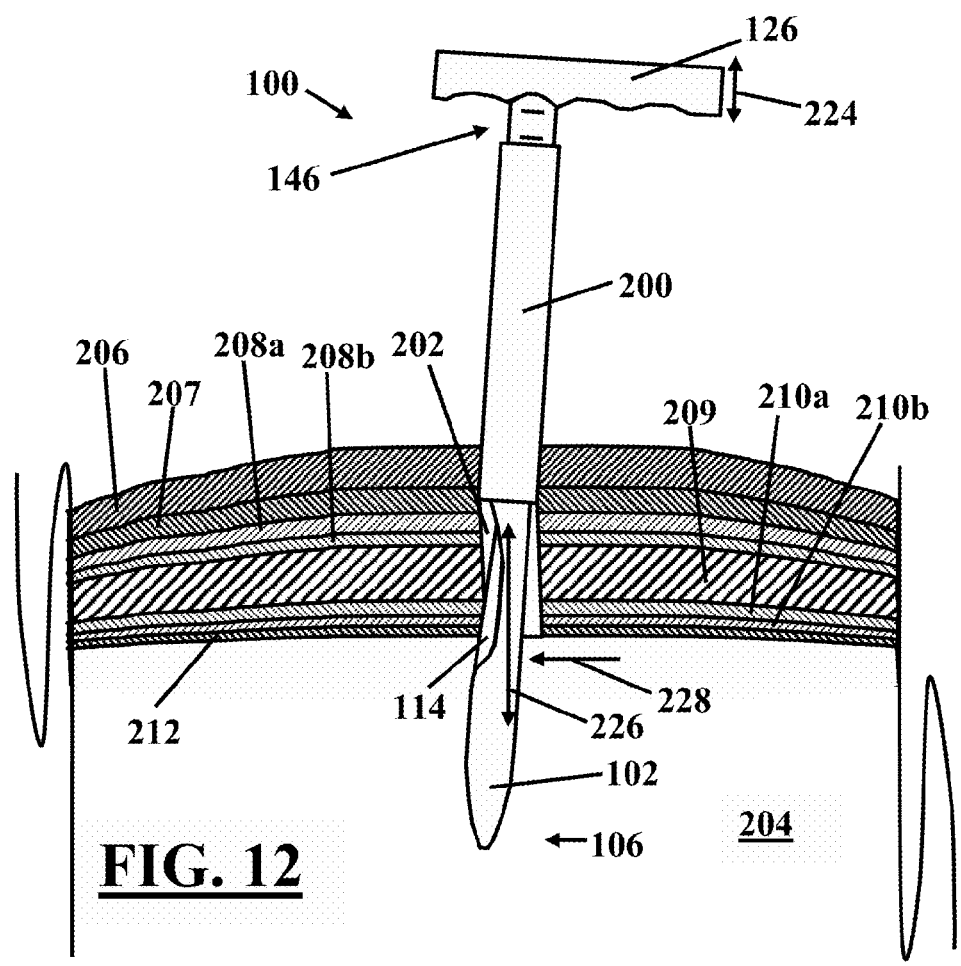
FIG. 12 illustrates an embodiment for enlarging a laparoscopic incision that includes a longitudinally reciprocating motion of the cutting edge.

In practice, such a pyramidal type incision 202 may be achieved with the laparoscopic scalpel 100 by application of one or more modes for cutting. In one embodiment, for example, referring to FIG. 11, the handle 126 of the laparoscopic scalpel 100 may be maneuvered laterally as illustrated by arrow 218 relative to the incision 202. Motion of the handle laterally 218 causes the laparoscopic scalpel 100 and the trocar 200 to pivot such that cutting edge 116 of the blade 114 moves to engage tissue in an opposite lateral direction as illustrated by arrow 222. Referring to FIG. 12, once so engaged in this embodiment, the handle 126 may be translated in a proximal reciprocating fashion, as illustrated by arrow 224 relative to the trocar 200 and the incision 202. Such motion allows the one or more of the peritoneum 212, the dorsal fascia layers 210, the muscle layers 209 and/or other layers as desired to be cut by moving the cutting edge 116 of the blade 114 relative to the incision 202 in a longitudinally reciprocating sawing type motion, as illustrated by arrow 226 in FIG. 12. Application of the longitudinally reciprocating or sawing type motion 226 effectively enlarges the incision 202 in the direction illustrated by arrow 228.

Figure 13:
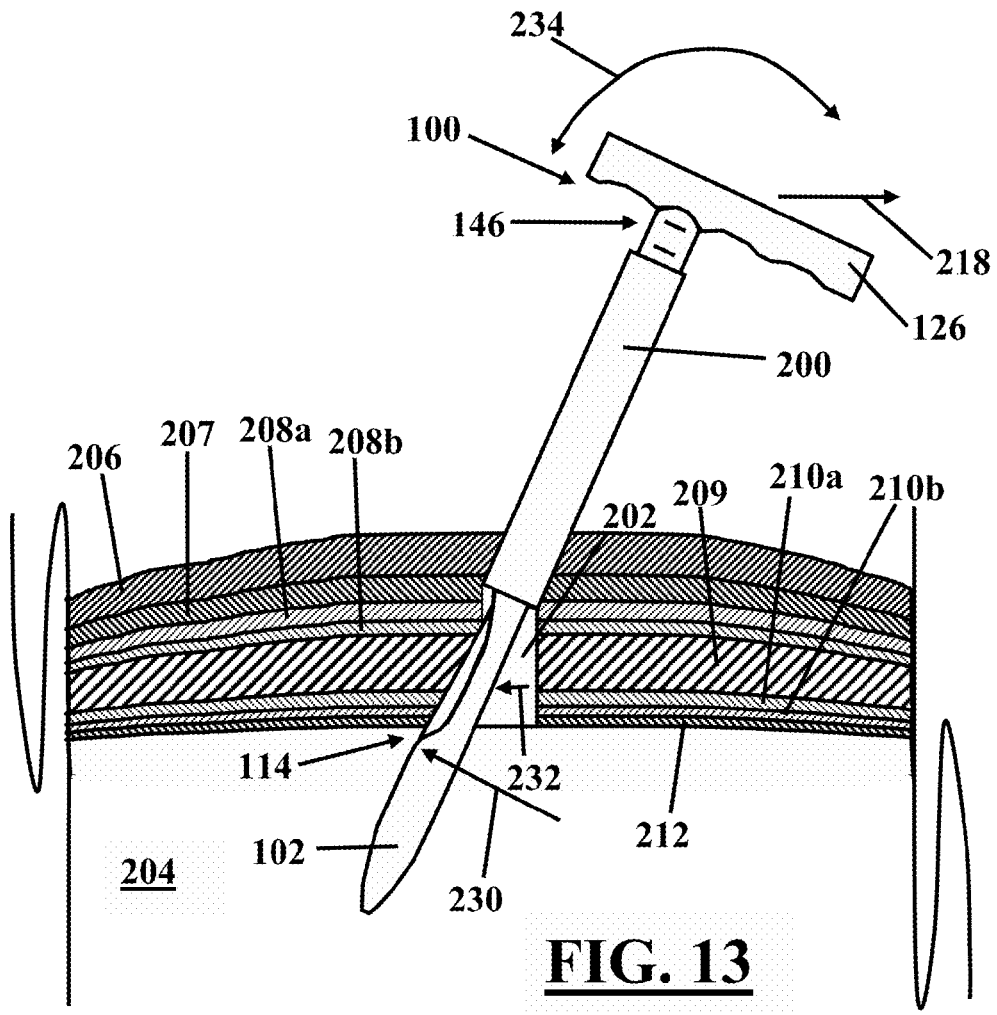
FIG. 13 illustrates an embodiment for enlarging a laparoscopic incision that includes a transverse slicing motion of the cutting edge.

In another embodiment, the cutting edge 116 is maneuvered into cutting engagement with tissue to be incised as described hereinabove with regard to FIG. 11. Referring to FIG. 13, in this embodiment, further motion of the handle laterally 218 causes the cutting edge 116 to cut tissue in a transverse slicing motion as indicated by arrow 230. Application of the cutting edge 116 in such transverse slicing motion 230 effectively enlarges the incision 202 in the direction illustrated by arrow 232.

In a further embodiment, referring to FIG. 13, a medical professional may gain additional control over the cutting by application of a combination of proximal and lateral motion to the handle 126 as illustrated by the arrow 234. Such combined motion applies both a longitudinal sawing motion 226 and a transverse slicing motion 230 of the cutting edge 116 to the tissue to be cut.

Thus, lateral 218 and/or proximal 224 motion of the handle 126 allows a surgeon to manipulate the cutting edge 116 to incise one or more of the layers of tissue 206, 207, 208a, 208b, 209, 210a, 210b, 212 as desired to enlarge the incision 202 without compromise of a patient's pneumoperitoneum. In this context, features of various embodiments of the laparoscopic scalpel 100 as described hereinabove may provide further advantage in enlarging the incision 202. For example, as noted hereinabove with regard to FIGS. 1-5, the proximal end 118 of the portion of the cutting edge 116 exposed by the recess 110 is disposed further from the surface 108 than is the distal end 120 of the portion of the cutting edge 116 exposed by the recess 110. In embodiments having a linear cutting edge 116, such configuration results in the non-zero angle 122 (See FIG. 2) between the cutting edge 116 and the surface 108. An instrument having a cutting edge generally aligned with the shaft of the instrument only allows for tissue to be incised at right angles to the shaft of the instrument. However, the blade 114 including the cutting edge 116 configured having a non-zero angle 122 with the surface 108 provides additional mechanical advantage to the surgeon allowing for precise control over the length and location of cuts made by the cutting edge 116 when manipulated via lateral motion 218, proximal motion 224, or a combination of proximal and lateral motion 234 of the handle 126. Such control facilitates precise incision of deeper tissue layers (for example, the peritoneum 212, the dorsal fascia layers 210, the layers of muscle 209, and the ventral fascia layers 208) while leaving the incision 202 through the skin layer 206 and the subcutaneous tissue layer 207 intact.

Referring to FIGS. 1-5, the recess 110 may have an unsymmetrical longitudinal shape that may provide additional mechanical advantage to the surgeon to facilitate precise control over the cutting edge 116. For example, a distal end 148 of the recess 110 may be oriented at a first angle 150 relative to the surface 108 and a proximal end 152 of the recess 110 may be oriented at a second angle 154 relative to the surface 108. The first angle 150 may be larger, the same as, or smaller than the second angle 154. Making the first angle 150 larger than the second angle 154, may, for example, allow the surgeon to precisely create the above described pyramidal type incision having the largest expanse at the most dorsal part of the abdominal wall and tapering up to a smallest expanse as it nears the skin layer 206. The different (larger angle) at the distal end 148 allows the action of the blade 114 to have better access for tissue penetration to create the desired incision at the deepest levels. Following enlargement of the laparoscopic incision 202, a surgeon may remove an organ or other tissue from the body cavity 204.

Existing methods for enlargement of a laparoscopic incision for removal of an organ or tissue sample are inadequate for several reasons. For example, because the incision 202 is bluntly spread or ripped apart using existing methods, and such spreading requires access by a surgeon's fingers, the trocar 200 is necessarily removed from the incision 202 prior to such spreading. Although the surgeon quickly plugs the incision 202 with a finger to preserve the pneumoperitoneum, removal of the trocar 200 causes some loss of the pneumoperitoneum, and the loss may result in a spray of fluid from the body cavity 204.

Next, the incision 202 through the skin 206 is typically lengthened to accommodate a second finger. Such lengthening of the incision 202 may result in additional loss of the pneumoperitoneum (and additional fluid expulsion from the body cavity 204). Next, a blunt instrument or two fingers are used to spread the incision 202 by ripping it open. In existing methods, the surgeon frantically attempts to get the incision 202 spread adequately before all gas pressure of the patient's pneumoperitoneum is lost.

Next, the trocar 200 is reinserted into the incision 202; however in existing methods such reinsertion is difficult because there is nothing to mark the exact location of the incision 202 or to guide the trocar 200 through the now raggedly enlarged incision 202, which may not follow a straight path into the body cavity 204. Upon reinsertion of the trocar 200, a grasping instrument may be inserted through the trocar 200 and visually guided to grasp hold of the tissue to be removed. With the tissue so grasped, the trocar 200 may need to be removed from the incision 202 a second time if the tissue is too large to be removed through the trocar 200. Such removal of the trocar 200 from the incision 202 may cause additional loss of the pneumoperitoneum through the raggedly enlarged incision 202. Next, the tissue is extracted via the raggedly enlarged incision 202, potentially causing further loss of the pneumoperitoneum.

Alternatively, using existing methods, some surgeons will controllably release the pneumoperitoneum (equalize pressure, for example, by opening a valve 160 (See FIG. 9) on the trocar 200) prior to a first removal of the trocar 200 from the incision 202 prior to the spreading thereof. However, the lengthened incision through the skin 206 and/or the ragged nature of the enlarged incision 202 caused by forced spreading or ripping thereof makes subsequent reestablishment of a pneumoperitoneum problematic.

In contrast to existing methods, by utilizing the apparatus and methods described hereinabove, the incision 202 may be more precisely enlarged below the skin layer 206. As noted hereinabove, precise enlargement also causes less postoperative pain, may heal faster, and provides better control over loss of the pneumoperitoneum. For example, in a first step, any embodiment of the laparoscopic scalpel 100 described hereinabove with regard to FIGS. 1-6 is introduced into a body cavity 204 via a trocar 200 that has a seal as described hereinabove with regard to FIG. 7. Next, the laparoscopic incision 202 is enlarged using any of the embodiments for enlargement of the incision described hereinabove with regard to FIGS. 8-13.

Next, a grasping instrument may be inserted through the trocar 200 to be visually guided to grasp hold of the tissue to be removed. With the tissue so grasped, the pneumoperitoneum may be slowly and controllably released by releasing the seal on the trocar 200. Such release may be accomplished, for example, by opening the valve 160 (See FIG. 9) on the trocar 200 to equalize pressure as known in the art. An outlet of the valve 160 may be connected to a containment system (not shown) to capture efflux of fluid released through the valve 160. Following controlled release of the pneumoperitoneum, the tissue is extracted via the enlarged incision 202.

If the tissue to be removed is small relative to the trocar 200, the tissue may be removed through the trocar 200. Alternatively, the trocar 200 is removed from the incision 202 to allow for removal of tissue therethrough. In this case, having an incision 202 that has not been lengthened at the skin layer 206 and that has been cleanly incised at more dorsal layers instead of being ripped open as in existing methods facilitates the maintenance of a seal between the incision 202 and the tissue being withdrawn. Next, the trocar 200 is reinserted into the incision 202 and the pneumoperitoneum may be reestablished. After satisfactory inspection of the surgical field, the surgeon next closes the enlarged incision 202.

Following enlargement of the laparoscopic incision 202, in lieu of or as a part of the process of removal of tissue from the body cavity 204, a surgeon may introduce a device into the body cavity 204. For example, the surgeon may introduce an intraluminal stapling device into the patient after enlarging the laparoscopic incision 202. A stapling device may sometimes be inserted into the body cavity 204 to divide tissue or to create a connection between viscera therein. However, some types of staplers such as, for example, a circular stapler, are too large to fit through the trocar 200. In order to operate such staplers laparoscopically, the incision 202 must be enlarged just enough to allow passage of the stapler, but not so much that the pneumoperitoneum cannot be preserved after the stapler is introduced. Using existing methods, as noted hereinabove, the incision 202 is enlarged by bluntly spreading the tissue layers apart with the surgeon's fingers or a blunt instrument. Such blunt spreading is imprecise and frequently leads to irregularly shaped holes which are more difficult to close and can result in hernia formation. The blunt dissection is also more traumatic and causes more post-operative swelling and pain than a precise incision.

In contrast, using the apparatus and methods described hereinabove with regard to FIGS. 1-13, an enlarged incision 202 may be created having a regularly and precisely shaped hole that is easier to close. Such a hole is also easier to plug with a finger when necessary, for example upon removal of the trocar 200 from the incision 202. Such a hole is also easier to maintain a seal with objects passed therethrough, for example, the trocar 200 or a stapler, or even tissue being removed therethrough. Following enlargement of the incision 202, for example, such a hole is created that may allow for removal of the trocar 200 and insertion of a finger into the incision 202 with minimal loss of the pneumoperitoneum (assuming there has been no equalization of pressure prior to removal of the trocar 200). Subsequently, a stapler or other device may be passed through the incision while maintaining a seal between the device and the incision. Alternatively, the stapler or other device may be passed through the trocar 200.

A laparoscopic scalpel useful for the enlargement of a laparoscopic incision without loss of a patient's pneumoperitoneum is presented. Such enlargement facilitates extraction of bigger specimens from a body cavity. Extraction of bigger specimens allows for wider applicability across multiple specialties, for example, including, but not limited to urology, gynecology, general surgery, bariatric surgery, endocrine surgery, colo-rectal surgery, liver surgery, and thoracoscopic surgery of the chest. Such enlargement further facilitates delivery of surgical devices, for example, intraluminal staplers, into the body cavity.

It will be appreciated by those skilled in the art that changes could be made to the embodiments described hereinabove without departing from the broad concepts disclosed therein. It is understood, therefore, that this disclosure is not limited to the particular embodiments disclosed, but it is intended to cover modifications that may include a combination of features illustrated in one or more embodiments with features illustrated in any other embodiments. Various modifications, equivalent processes, as well as numerous structures to which the present disclosure may be applicable will be readily apparent to those of skill in the art to which the present disclosure is directed upon review of the present specification. Accordingly, this description is to be construed as illustrative only and is presented for the purpose of enabling those skilled in the art to make and use the laparoscopic scalpel described herein and to teach the best mode of carrying out the same.

What is claimed is:

1. A laparoscopic scalpel, comprising:
a shaft having a proximal end, a distal end, and a length there between;
a recess disposed in a surface of the shaft, the recess having a proximal end and a distal end along the length of the shaft wherein the distal end of the recess is disposed proximal to the distal end of the shaft; and
a blade attached to the shaft, wherein the blade includes a cutting edge having a portion exposed by the recess and oriented outwardly from the recess, and wherein a proximal end of the portion of the cutting edge exposed by the recess is disposed further from a straight line between the distal and proximal ends of the recess than is a distal end of the portion of the cutting edge exposed by the recess.

2. The laparoscopic scalpel of claim 1, further comprising an edge guide disposed longitudinally along the surface of the shaft generally aligned with the cutting edge.

3. The laparoscopic scalpel of claim 2, further comprising a handle oriented transversely to the shaft and disposed on a proximal end thereof.

4. The laparoscopic scalpel of claim 3, wherein the handle is detachably attached to the shaft.

5. The laparoscopic scalpel of claim 3, wherein the handle extends from the shaft in a direction that is generally normal to the edge guide.

6. The laparoscopic scalpel of claim 3, further including finger grips disposed on the handle.

7. The laparoscopic scalpel of claim 1, wherein the cutting edge includes serrations.

8. The laparoscopic scalpel of claim 1, further comprising a blunt end surface at the distal end of the shaft.

9. The laparoscopic scalpel of claim 8, wherein a portion of the shaft that is A proximal to the blunt end comprises a cross-sectional shape selected from a group of cross-sectional shapes consisting of: generally circular, elliptical, oval, regular polygonal, and irregular polygonal.

10. The laparoscopic scalpel of claim 1, wherein a distal surface of the recess is oriented at a first angle relative to said straight line and a proximal surface of the recess is oriented at a second angle relative to said straight line, and wherein the first angle is larger than the second angle.

11. The laparoscopic scalpel of claim 1, further comprising a tapered portion disposed at a proximal end of the shaft.

12. The laparoscopic scalpel of claim 1, further comprising a compressible surface region disposed at a proximal end of the shaft.

13. A laparoscopic scalpel, comprising:
a shaft;
a recess having a proximal end and a distal end, the recess disposed in a surface of the shaft such that the distal end of the recess is disposed proximal to a distal end of the shaft, wherein a portion of the surface of the shaft is replaced by the recess; and
a blade attached to the shaft, wherein the blade includes a cutting edge having a portion exposed by the recess and oriented outwardly from the recess, and wherein a proximal end of the portion of the cutting edge exposed by the recess is disposed further from a straight line between the distal and proximal ends of the recess than is a distal end of the portion of the cutting edge exposed by the recess; and
a handle disposed on a proximal end of the shaft and extending from the shaft along a plane that is generally parallel to the cutting edge.

14. The laparoscopic scalpel of claim 13, wherein the shaft is adapted to be inserted through a trocar into a patient while generally maintaining a patient's pneumoperitoneum.

15. The laparoscopic scalpel of claim 14, wherein the distal end of the shaft includes a blunt end surface adapted to allow for safe placement of the scalpel through the trocar without visual guidance.

16. The laparoscopic scalpel of claim 15, wherein the shaft includes regularly spaced distance markings disposed along the surface thereof and adapted to indicate depth of insertion of the shaft when inserted through the trocar.

17. The laparoscopic scalpel of claim 16, further comprising an edge guide disposed on an edge of the handle in general alignment with the cutting edge.

18. The laparoscopic scalpel of claim 17, further including the trocar.

19. A method for using a laparoscopic scalpel including a shaft, a recess having a proximal end and a distal end, the recess disposed in a surface of the shaft such that the distal end of the recess is disposed proximal to a distal end of the shaft, and a blade attached to the shaft, wherein the blade includes a cutting edge having a portion exposed by the recess and oriented outwardly from the recess, and wherein a proximal end of the portion of the cutting edge exposed by the recess is disposed further from a straight line between the distal and proximal ends of the recess than is a distal end of the portion of the cutting edge exposed by the recess, and wherein the shaft is adapted to be inserted through a trocar into a patient, the method including the steps of:

- inserting the distal end of the shaft into a trocar disposed within a laparoscopic incision;
- translating the trocar proximally relative to the shaft to expose one or more of the peritoneum, dorsal fascia, muscle, ventral fascia, and subcutaneous tissue to the cutting edge while generally maintaining a patient's pneumoperitoneum; and
- cutting the one or more of the peritoneum, dorsal fascia, muscle, ventral fascia, and subcutaneous tissue with the cutting edge to enlarge the laparoscopic incision without compromise of the patient's pneumoperitoneum.

20. The method of claim 19, further including the step of orienting the cutting edge rotationally as desired within the trocar.

* * * * *